United States Patent
Wang et al.

(10) Patent No.: US 10,131,625 B2
(45) Date of Patent: Nov. 20, 2018

(54) METHOD FOR PREPARING 3-CARBAMOYMETHYL-5-METHYLHEXANOIC ACID IN RECYCLING WAY

(71) Applicant: Zhejiang Huahai Pharmaceutical Co., Ltd., Zhejiang (CN)

(72) Inventors: Shudong Wang, Zhejiang (CN); Xuehai You, Zhejiang (CN); Wenling Zhang, Zhejiang (CN)

(73) Assignee: Zhejiang Huahai Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 15/521,021

(22) PCT Filed: Oct. 13, 2015

(86) PCT No.: PCT/CN2015/091836
§ 371 (c)(1),
(2) Date: Apr. 21, 2017

(87) PCT Pub. No.: WO2016/062212
PCT Pub. Date: Apr. 28, 2016

(65) Prior Publication Data
US 2017/0334836 A1    Nov. 23, 2017

(30) Foreign Application Priority Data
Oct. 24, 2014    (CN) .......................... 2014 1 0589184

(51) Int. Cl.
*C07C 235/12* (2006.01)
*C07C 233/05* (2006.01)
*C07C 231/24* (2006.01)
*C07C 211/27* (2006.01)
*C01D 1/04* (2006.01)

(52) U.S. Cl.
CPC .......... *C07C 235/12* (2013.01); *C07C 211/27* (2013.01); *C07C 231/24* (2013.01); *C07C 233/05* (2013.01); *C01D 1/04* (2013.01); *Y02P 20/582* (2015.11)

(58) Field of Classification Search
CPC ................................................ C07C 231/24
See application file for complete search history.

(56) References Cited

FOREIGN PATENT DOCUMENTS

| CN | 101500985 A | 8/2009 |
| CN | 103980144 A | 8/2014 |
| CN | 104086439 A | 10/2014 |
| CN | 104356016 A | 2/2015 |
| WO | WO 96/38405 A1 | 12/1996 |
| WO | WO 2011/077463 A1 | 6/2011 |

OTHER PUBLICATIONS

Chaven et al, Organic Process Research & Development, An Efficient Process of Racemization of 3-(Carbamoylmethyl)-5-methylhexanoic Acid: A Pregabalin Intermediate, 2009, 13, pp. 812-814. (Year: 2009).*
Zaragoza Dorwald, Side Reactions in Organic Synthesis, 2005, WILEY-VCH Verlag GmbH & Co. KGaA, Weinheim, Preface. p. IX. (Year: 2005).*
Chavan et al, OrganicProcess Research & Development, An Efficient Process of Racemization of 3-(Carbamoylmethyl)-5-methylhexanoic Acid: A Pregabalin Intermediate, 2009, 13, pp. 812-814. (Year: 2009).*
International Search Report and Written Opinion dated Jan. 18, 2016, in connection with PCT/CN2015/091836.
Chavan, et al., An efficient process of racemization of 3-(carbamoylmethyl)-5-methylhexanoic acid: a pregabalin intermediate. Org. Process Res. Dev., 2009; 13(4): 812-14. doi: 10.1021/op900064x.

* cited by examiner

*Primary Examiner* — Paul A Zucker
(74) *Attorney, Agent, or Firm* — Wolf, Greenfield & Sacks, P.C.

(57) ABSTRACT

The present invention provides a method for recycling 3-carbamoylmethyl-5-methylhexanoic acid from 3-carba carbamoylmethyl moymethyl-5-methylhexanoic acid chiral resolving mother liquor. The method comprises the following steps: (a) distilling 3-carbamoylmethyl-5-methylhexanoic acid chiral resolving mother liquor, adding aromatic hydrocarbon, heating to dissolve, keeping the temperature and stirring; (b) after completing the reaction in step (a), cooling the reaction solution to 30-60° C., then adding alkali liquor dropwise, keeping the temperature and reacting; and (c) after completing the reaction in step (b), cooling the reactant to 20-30° C., layering, adjusting the pH of the separated water layer to 1 to 2, performing extraction by using an organic solvent, distilling an organic phase under a reduced pressure, and crystallizing at 0±5° C. to obtain 3-carbamoylmethyl-5-methylhexanoic acid. The method provided in the present invention is convenient to operate, and the recycled product is high in purity (≥99.8%) and yield.

18 Claims, No Drawings

METHOD FOR PREPARING 3-CARBAMOYMETHYL-5-METHYLHEXANOIC ACID IN RECYCLING WAY

CROSS REFERENCE TO RELATED APPLICATIONS

The present application is the National Phase under 35 U.S.C. § 371 of PCT International Application No. PCT/CN2015/091836, filed Oct. 13, 2015, which claims the priority of a Chinese Patent Application No. 201410589184.X titled "METHOD FOR PREPARING 3-CARBAMOYMETHYL-5-METHYLHEXANOIC ACID IN RECYCLING WAY", filed on Oct. 24, 2014 before the State Intellectual Property Office of China, which applications are incorporated herein by reference in their entirety.

FIELD OF THE INVENTION

The present application relates to a method for recycling a pharmaceutical intermediate, and in particular to a method for recycling 3-carbamoylmethyl-5-methylhexanoic acid, a key intermediate of Pregabalin, from the chiral resolving mother liquor of 3-carbamoylmethyl-5-methylhexanoic acid.

BACKGROUND OF THE INVENTION

Pregabalin, a new type antagonist of γ-aminobutyric acid (GABA) receptor, is developed by Pfizer. It was approved by European Union for the first time in July 2004 for treating partial seizure in adult patients, and the trade name thereof is Lyrica. In June 2005, it was approved for sale in the US by US Food and Drug Administration (FDA). Indications thereof were added in March 2006 for treating generalized anxiety disorder and social anxiety disorder. In 2009, it was approved additionally for treating spinal cord injury, trauma, multiple sclerosis, diabetic neuropathic pain and shingles neuropathic pain, which further extends its clinical application. Since Pregabalin has good effects on anti-epilepsy, anti-anxiety and treating neuropathic pain and the like, it has been widely used in clinical treatment currently, and the market demand further increased. According to a survey, Pregabalin on the market is mostly synthesized by using the method of chemical synthesis currently.

The 3-carbamoylmethyl-5-methylhexanoic acid is a key intermediate for preparing Pregabalin, and the structure formula thereof is shown as follow.

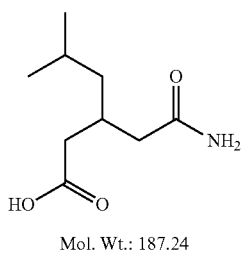

Mol. Wt.: 187.24

In the process of preparing Pregabalin, the (S) type isomer of 3-carbamoylmethyl-5-methylhexanoic acid is used. Currently, most of the literatures have reported this levoisomer is obtained by using a resolution method with a resolving agent. However, the yield of resolving 3-carbamoylmethyl-5-methylhexanoic acid to (S)-3-carbamoylmethyl-5-methylhexanoic acid is only about 35%, and a great quantity of raw materials remain in the resolving mother liquor (i.e., the utilization rate of 3-carbamoylmethyl-5-methylhexanoic acid is about 35%). When Pregabalin is produced commercially on large scale, about 65% of the intermediate will remain in the mother liquor if not considering the recycle of mother liquor, which results in waste, and thereby enormously increases the cost for producing Pregabalin. In India Anil B. Chavan et al. mentioned reusing 3-carbamoylmethyl-5-methylhexanoic acid in the mother liquor by using a racemization recycle method in the article "An Efficient Process of Racemization of 3-(Carbamoylmethyl)-5-methylhexanoic acid: A Pregabalin Intermediate" (see *Organic process research and Development*, Vol 13, No. 4, Page 812-814, May 18, 2009). In such methods, alkali liquor is usually added into mother liquor at first, layered, and then pH is adjusted. The wet product is filtered, then toluene is added, and then diisopropylamine, 1,8-diazabicyclo-undec-7-ene (DBU), diisopropylethylamine and the like are added to reflux and react for racemization. Then alkali is used for the ring-opening reaction, pH is adjusted, and the reactant is filter, refine by ethyl acetate, and dry (total yield: about 50% by the amount of 3-carbamoylmethyl-5-methylhexanoic acid added in the resolution). This method is cumbersome and lengthy, and the operation is complicated, requiring twice pH adjustment, which introduces large quantity of inorganic salts, and produces waste water.

SUMMARY OF THE INVENTION

The object of the present invention is to provide a method for recycling 3-carbamoylmethyl-5-methylhexanoic acid from 3-carbamoylmethyl-5-methylhexanoic acid chiral resolving mother liquor. This method is suitable for industrial production, and increases the utilization rate of 3-carbamoylmethyl-5-methylhexanoic acid, thereby reduces the cost of production.

In the present invention, 3-carbamoylmethyl-5-methylhexanoic acid chiral resolving mother liquor is distilled directly. After distilling, aromatic hydrocarbon solvent such as toluene, p-xylene and the like, is added to directly reflux to remove water. It is racemized, crystallized, filtered and dried to obtain the final product. The method of the present invention enormously reduces the operation steps, simplifies the technical processes, reduces the loss, increases the utilization rate of raw materials (the total utilization rate of 3-carbamoylmethyl-5-methylhexanoic acid is 70-80% after improvement), reduces the cost, protects the environment, and is atom economic. It is suitable for commercial production.

More specifically, the present invention provides a method of recycling 3-carbamoylmethyl-5-methylhexanoic acid of high purity from 3-carbamoylmethyl-5-methylhexanoic acid chiral resolving mother liquor, comprising following steps:

(a) distilling 3-carbamoylmethyl-5-methylhexanoic acid chiral resolving mother liquor, then adding aromatic hydrocarbon, heating to dissolve, keeping the temperature and stirring;

(b) after completing the reaction in the above step (a), cooling the above reaction solution, then adding alkali liquor dropwise, keeping the temperature and reacting; and (c) after completing the reaction in the above step (b), cooling to 20-30° C., layering, adjusting the pH of the separated water layer to 1-2, extracting with organic solvents, distilling the organic phase under reduced pressure, and then crystallizing at a temperature of 0±5° C. to obtain 3-carbamoylmethyl-5-methylhexanoic acid.

In one embodiment according to the method of the present invention, said 3-carbamoylmethyl-5-methylhexanoic acid chiral resolving mother liquor in step (a) is the mother liquor obtained by centrifuging and filtering after the resolution of 3-carbamoylmethyl-5-methylhexanoic acid with a resolution agent (R-phenylethylamine).

In one embodiment according to the method of the present invention, the aromatic hydrocarbon added into 3-carbamoylmethyl-5-methylhexanoic acid chiral resolving mother liquor after the distilling in step (a) is $C_6$-$C_{12}$ aromatic hydrocarbon; preferably benzene, toluene, xylene or p-xylene; and more preferably toluene or xylene.

In one embodiment according to the method of the present invention, the temperature for heating to dissolve in step (a) is 80-150° C., further preferably 100-120° C.

In one embodiment according to the method of the present invention, after said distilling in step (a), the ratio of the mass of 3-carbamoylmethyl-5-methylhexanoic acid chiral resolving mother liquor to the volume of aromatic hydrocarbon solvent is 1:10-1:20 g/ml, preferably 1:13-1:18 g/ml.

In one embodiment according to the method of the present invention, the temperature of the reaction in step (a) is 90-130° C., further preferably 100-120° C.

In one embodiment according to the method of the present invention, the duration of the reaction in step (a) is 20-48 h, further preferably 24-34 h.

In one embodiment according to the method of the present invention, the temperature of the reaction in step (b) is 90-130° C., further preferably 100-120° C.

In one embodiment according to the method of the present invention, the duration of the reaction in step (b) is 20-48 h, further preferably 24-34 h.

In one embodiment according to the method of the present invention, the final temperature of said cooling in step (b) is 30-60° C., further preferably 40-50° C.

In one embodiment according to the method of the present invention, said alkali liquor in step (b) is aqueous solution of alkali metal hydroxide and/or aqueous solution of alkali metal carbonate, such as aqueous solution of sodium hydroxide, sodium carbonate, potassium carbonate, or potassium hydroxide, preferably aqueous solution of sodium hydroxide or potassium carbonate, and the concentration of the mass percentage of the alkali liquor is preferably 20-30%.

In one embodiment according to the method of the present invention, the amount of the alkali liquor used in step (b) is 1-3 times, further preferably 2-3 times of the content of 3-carbamoylmethyl-5-methylhexanoic acid in 3-carbamoylmethyl-5-methylhexanoic acid chiral resolving mother liquor (mass ratio, by the amount of 3-carbamoylmethyl-5-methylhexanoic acid before resolution).

In one embodiment according to the method of the present invention, said alkali liquor in step (b) is added dropwise at a temperature of 30-60° C., further preferably 30-50° C.

In one embodiment according to the method of the present invention, the cooling in step (b) is carried out at a cooling rate of 1° C. per 5 minutes, and the crystallization time is controlled in the range of 3-5 hours.

In one embodiment according to the method of the present invention, the final temperature of said cooling in step (b) is 40-50° C.

In one embodiment according to the method of the present invention, the cooling after the distillation under reduced pressure in step (c) is carried out at a cooling rate of 1° C. per 5 minutes, and the crystallization time is controlled in the range of 3-5 hours.

In one embodiment according to the method of the present invention, the solvent for extracting in step (c) is organic solvent that is water-immiscible, preferably selected from n-hexane, cyclohexane, n-heptane, toluene, ethyl acetate or ethyl ether, further preferably n-heptane, ethyl acetate or toluene.

In the reaction formula of preparing Pregabalin from 3-carbamoylmethyl-5-methylhexanoic acid, the present invention relates to recycling reactant of 3-carbamoylmethyl-5-methylhexanoic acid exemplified as follows:

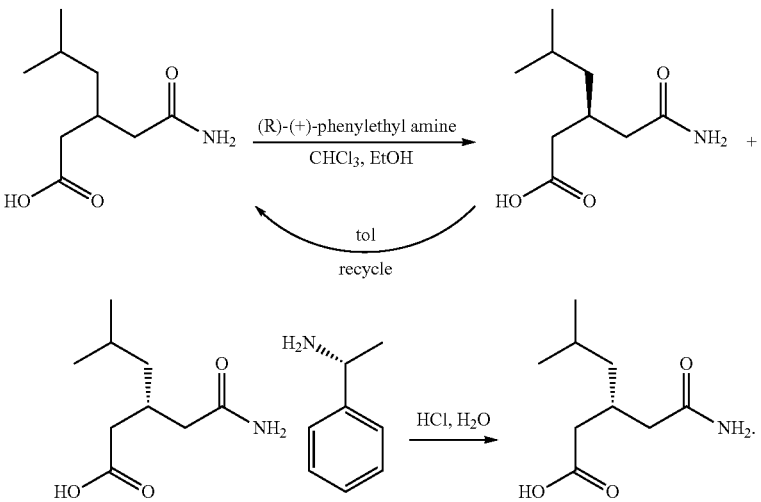

The purification method provided by the present invention is easy to operate with low operating cost; the quality of products obtained is good, the 3-carbamoylmethyl-5-methylhexanoic acid after refining is white, with purity (HPLC) ≥99.8%, which can satisfy the requirements of high quality intermediate for the production of Pregabalin.

DETAILED DESCRIPTION OF THE INVENTION

To make the objects, technical solutions, and advantages of the present invention much more clearly, hereinafter the present invention will be further described in detail by referring to the examples. It is obvious that the described examples are only parts of examples of the present invention, rather than all of the examples. Based on the examples in the present invention, any other examples that obtained without creative work by the ordinary skilled in the art are within the protection scope of the present invention.

Definition

The aromatic hydrocarbon used in the present invention refers to hydrocarbons containing benzene ring structure in the molecule, in particular to $C_6$-$C_{12}$ aromatic hydrocarbons, and includes but not limited to, benzene, toluene, xylene, p-xylene, o-xylene, m-xylene, ethylbenzene, isopropyl benzene, naphthalene and the like.

The xylene used in the present invention means the mixture of three isomers of o-xylene, m-xylene and p-xylene.

Reference Example: Obtaining 3-carbamoylmethyl-5-methylhexanoic Acid Mother Liquor 2139.0 g of trichloromethane and 26.7 g of ethanol were pumped into a 3 L reaction kettle in order under the temperature of 15-25° C., and 142.0 g of 3-carbamoylmethyl-5-methylhexanoic acid was added under stirring by a solid feeder. The feeder was washed with 300.0 g of trichloromethane. The kettle was heated to 55-60° C. within 1-2 hours. 50.0 g of R(+)-α-phenethylamine was added dropwise at 55-60° C. during about 3-4 hours, and stirred continuously for 0.5-1 hour at 55-60° C. 16.7 g of R(+)-α-phenethylamine was added dropwise at 55-60° C. during about 2-3 hours, and stirred continuously for 1-2 hours at 55-60° C. after completion of the dropping. The kettle was cooled to 28-32° C. at a cooling rate of 10-20° C./hour. The stir was continued for 1-2 hours at 28-32° C. The reaction product was filtered at 28-32° C., the wet filter cake was washed twice with 184.0 g of trichloromethane, and the filtrates were combined, and reserved for later use.

Example 1: Recycling 3-carbamoylmethyl-5-methylhexanoic Acid from 3-carbamoylmethyl-5-methylhexanoic Acid Chiral Resolving Mother Liquor The filtrate (about 1.7 L) obtained in the above reference example was pumped in, and concentrated to 300-500 mL under reduced pressure while controlling the temperature to 30-40° C. The concentrate was cooled to 15-25° C., and 200 mL of water was added. The reactant was concentrated under reduced pressure while controlling the temperature to 30-40° C. until no obvious distillate flowed out. 700 mL of toluene was added, and the temperature was raised to 110-120° C. within 1-2 hours with stirring, and water was removed at the same time. HPLC detection was conducted every 4 hours from the $24^{th}$ hour until the amount of 3-carbamoylmethyl-5-methylhexanoic acid was <1%. The temperature was cooled to 40-50° C. within 1-2 hours. 284.0 g of water and 284.0 g of 10% aqueous solution of NaOH were added dropwise at 40-50° C., and the temperature was controlled at 35-55° C. The reactant was stirred at 40-50° C. for 3-4 hours, then cooled to 20-30° C., and stood to layer for 1-2 hours. The liquids were separated, after the water phase was separated, 140.0 g of water was added into the organic phase, stirred for 0.5-1 hour and stood and layered for 1-2 hours. The liquids were separated. After separation the water phases were combined. 167.0 g of toluene was added into the water phase, stirred for 0.5-1 hour and stood to layer for 0.5-1 hour. The liquids were separated. 167.0 g of toluene was added into the water phase, stirred for 0.5-1 hour and stood to layer for 0.5-1 hour. The water phase was separated. 100.0 g of concentrated hydrochloric acid was added into the water phase dropwise to adjust the pH to 1.5-2 (took the amount of concentrated hydrochloric acid added as the practical dosage), and the temperature was controlled at 0-10° C. It was stirred for 1-2 hours at 0-5° C. 600 mL of ethyl acetate was added, and stirred for 20-30 minutes and stood to layer for 30 minutes. Then 300 mL of ethyl acetate was added into the water phase, stirred for 20-30 minutes and stood to layer for 30 minutes. The organic phases were combined and distilled to 240 mL under a reduced pressure at 40-50° C., and cooled slowly to 0±5° C., filtered, and dried. 3-carbamoylmethyl-5-methylhexanoic acid was recycled once (about 67.9 g of white solid, with the yield of 72.5%, and the purity of 99.81%).

Example 2: Recycling 3-carbamoylmethyl-5-methylhexanoic Acid from 3-carbamoylmethyl-5-methylhexanoic Acid Chiral Resolving Mother Liquor The filtrate (about 1.7 L) obtained in the above reference example was pumped in, and concentrated to 300-500 mL under reduced pressure while controlling the temperature to 30-40° C. The concentrate was cooled to 15-25° C., and 200 mL of water was added. The reactant was concentrated under reduced pressure while controlling the temperature to 30-40° C. until no obvious distillate flowed out. 700 mL of xylene was added, and the temperature was raised to 110-120° C. within 1-2 hours with stirring, and water was removed at the same time. HPLC detection was conducted every 4 hours from the $24^{th}$ hour until the amount of 3-carbamoylmethyl-5-methylhexanoic acid was <1%. The temperature was cooled to 40-50° C. within 1-2 hours. 284.0 g of water and 284.0 g of 10% aqueous solution of NaOH were added dropwise at 40-50° C., and the temperature was controlled at 35-55° C. The reactant was stirred at 40-50° C. for 3-4 hours, then cooled to 20-30° C., and stood to layer for 1-2 hours. The liquids were separated, after the water phase was separated, 140.0 g of water was added into the organic phase, stirred for 0.5-1 hour and stood and layered for 1-2 hours. The liquids were separated. After separation the water phases were combined. 167.0 g of toluene was added into the water phase, stirred for 0.5-1 hour and stood to layer for 0.5-1 hour. The liquids were separated. 167.0 g of toluene was added into the water phase, stirred for 0.5-1 hour and stood to layer for 0.5-1 hour. The water phase was separated. 100.0 g of concentrated hydrochloric acid was added into the water phase dropwise to adjust the pH to 1.5-2 (took the amount of concentrated hydrochloric acid added as the practical dosage), and the temperature was controlled at 0-10° C. It was stirred for 1-2 hours at 0-5° C. 600 mL of n-heptane was added, and stirred for 20-30 minutes and stood to layer for 30 minutes. Then 300 mL of n-heptane was added into the water phase, stirred for 20-30 minutes and stood to layer for 30 minutes. The organic phases were combined and distilled to 240 mL under a reduced pressure at 60-70° C., and cooled slowly to 0±5° C., filtered, and dried. 3-carbamoylmethyl-5-methylhexanoic acid was recycled once (about 67.3 g of white solid, with the yield of 71.8%, and the purity of 99.79%).

Example 3: Recycling 3-carbamoylmethyl-5-methylhexanoic Acid from 3-carbamoylmethyl-5-methylhexanoic Acid Chiral Resolving Mother Liquor The filtrate (about 1.7 L) obtained in the above reference example was pumped in, and concentrated to 300-500 mL under reduced pressure while controlling the temperature to 30-40° C. The concentrate was cooled to 15-25° C., and 200 mL of water was added. The reactant was concentrated under reduced pressure while controlling the temperature to 30-40° C. until no obvious distillate flowed out. 700 mL of p-xylene was added, and the temperature was raised to 110-120° C. within 1-2 hours with stirring, and water was removed at the same time. HPLC detection was conducted every 4 hours from the $24^{th}$ hour until the amount of 3-carbamoylmethyl-5-methylhexanoic acid was <1%. The temperature was cooled to 40-50° C. within 1-2 hours. 284.0 g of water and 284.0 g of 10% aqueous solution of NaOH were added dropwise at 40-50° C., and the temperature was controlled at 35-55° C. The reactant was stirred at 40-50° C. for 3-4 hours, then cooled to 20-30° C., and stood to layer for 1-2 hours. The liquids were separated, after the water phase was separated, 140.0 g of water was added into the organic phase, stirred for 0.5-1 hour and stood and layered for 1-2 hours. The liquids were separated. After separation the water phases were combined. 167.0 g of toluene was added into the water phase, stirred for 0.5-1 hour and stood to layer for 0.5-1 hour. The liquids were separated. 167.0 g of toluene was added into the water phase, stirred for 0.5-1 hour and stood to layer for 0.5-1 hour. The water phase was separated. 100.0 g of concentrated hydrochloric acid was added into the water phase dropwise to adjust the pH to 1.5-2 (took the amount of concentrated hydrochloric acid added as the practical dosage), and the temperature was controlled at 0-10° C. It was stirred for 1-2 hours at 0-5° C. 600 mL of cyclohexane was added, and stirred for 20-30 minutes and stood to layer for 30 minutes. Then 300 mL of cyclohexane was added into the water phase, stirred for 20-30 minutes and stood to layer for 30 minutes. The organic phases were combined and distilled to 240 mL under a reduced pressure at 40-50° C., and cooled slowly to 0±5° C., filtered, and dried. 3-carbamoylmethyl-5-methylhexanoic acid was recycled once (about 66.9 g of white solid, with the yield of 70.5%, and the purity of 99.84%).

Example 4: Recycling 3-carbamoylmethyl-5-methylhexanoic Acid from 3-carbamoylmethyl-5-methylhexanoic Acid Chiral Resolving Mother Liquor The filtrate (about 1.7 L) obtained in the above reference example was pumped in, and concentrated to 300-500 mL under reduced pressure while controlling the temperature to 30-40° C. The concentrate was cooled to 15-25° C., and 200 mL of water was added. The reactant was concentrated under reduced pressure while controlling the temperature to 30-40° C. until no obvious distillate flowed out. 700 mL of p-xylene was added, and the temperature was raised to 110-120° C. within 1-2 hours with stirring, and water was removed at the same time. HPLC detection was conducted every 4 hours from the $24^{th}$ hour until the amount of 3-carbamoylmethyl-5-methylhexanoic acid was <1%. The temperature was cooled to 40-50° C. within 1-2 hours. 284.0 g of water and 284.0 g of 10% aqueous solution of NaOH were added dropwise at 40-50° C., and the temperature was controlled at 35-55° C. The reactant was stirred at 40-50° C. for 3-4 hours, then cooled to 20-30° C., and stood to layer for 1-2 hours. The liquids were separated, after the water phase was separated, 140.0 g of water was added into the organic phase, stirred for 0.5-1 hour and stood and layered for 1-2 hours. The liquids were separated. After separation the water phases were combined. 167.0 g of toluene was added into the water phase, stirred for 0.5-1 hour and stood to layer for 0.5-1 hour. The liquids were separated. 167.0 g of toluene was added into the water phase, stirred for 0.5-1 hour and stood to layer for 0.5-1 hour. The water phase was separated. 100.0 g of concentrated hydrochloric acid was added into the water phase dropwise to adjust the pH to 1.5-2 (took the amount of concentrated hydrochloric acid added as the practical dosage), and the temperature was controlled at 0-10° C. It was stirred for 1-2 hours at 0-5° C. 600 mL of ethyl acetate was added, and stirred for 20-30 minutes and stood to layer for 30 minutes. Then 300 mL of ethyl acetate was added into the water phase, stirred for 20-30 minutes and stood to layer for 30 minutes. The organic phases were combined and distilled to 240 mL under a reduced pressure at 40-50° C., and cooled slowly to 0±5° C., filtered, and dried. 3-carbamoylmethyl-5-methylhexanoic acid was recycled once (about 75.1 g of white solid, with the yield of 80.1%, and the purity of 99.81%). The above examples are only the preferable examples of the present invention, not intending to limit the present invention. Any modification, equivalent substitution, improvement and the like made within the spirit and principle of the present invention should be included in the protection scope of the present invention.

What is claimed is:

1. A method for recycling 3-carbamoylmethyl-5-methylhexanoic acid from 3-carbamoylmethyl-5-methylhexanoic acid chiral resolving mother liquor, comprising following steps:
   (a) distilling the 3-carbamoylmethyl-5-methylhexanoic acid chiral resolving mother liquor to obtain residues, then adding $C_6$-$C_{12}$ aromatic hydrocarbon, heating to dissolve the residues, keeping the temperature at 90-130° C. and stirring;
   (b) after completing reaction in the above step (a), cooling reaction solution to 30-60° C., then adding alkali liquor dropwise, keeping the temperature at 90-130° C. and reacting; and
   (c) after completing reaction in the above step (b), cooling to 20-30° C., layering, adjusting the pH of the separated water layer to 1-2, extracting with organic solvent, distilling the organic phase under reduced pressure, and then crystallizing at a temperature of 0±5° C. to obtain 3-carbamoylmethyl-5-methylhexanoic acid.

2. The method according to claim 1, characterized in that temperature for heating to dissolve the residues in step (a) is 80-150° C.

3. The method according to claim 1, characterized in that after the distilling in step (a), the ratio of the mass of 3-carbamoylmethyl-5-methylhexanoic acid chiral resolving mother liquor to the volume of aromatic hydrocarbon solvent is 1:10-1:20 g/ml.

4. The method according to claim 1, characterized in that the duration of the reaction in step (a) is 20-48 h.

5. The method according to claim 1, characterized in that the duration of the reaction in step (b) is 20-48 h.

6. The method according to claim 1, characterized in that the alkali liquor in step (b) is aqueous solution of alkali metal hydroxide and/or aqueous solution of alkali metal carbonate.

7. The method according to claim 1, characterized in that the alkali liquor in step (b) is added dropwise at a temperature of 30-50° C.

8. The method according to claim 1, characterized in that the final temperature of the cooling in step (b) is 40-50° C.

9. The method according to claim 1, characterized in that the cooling after distillation under reduced pressure in step (b) is carried out at a cooling rate of 1° C. per 5 minutes, and the crystallization time is controlled in the range of 3-5 hours.

10. The method according to claim 1, characterized in that the solvent for extracting in step (c) is organic solvent that is water-immiscible.

11. The method according to claim 1, characterized in that in the step (b), the mass ratio of the amount of the alkali liquor used to the content of the 3-carbamoylmethyl-5-methylhexanoic acid in the 3-carbamoylmethyl-5-methylhexanoic acid chiral resolving mother liquor is 1-3:1.

12. The method according to claim 1, characterized in that in the step (a), the 3-carbamoylmethyl-5-methylhexanoic acid chiral resolving mother liquor is the mother liquor obtained by centrifuging and filtering after the resolution of 3-carbamoylmethyl-5-methylhexanoic acid via a resolution agent of R-phenylethylamine.

13. The method according to claim 1, characterized in that the aromatic hydrocarbon added into 3-carbamoylmethyl-5-methylhexanoic acid chiral resolving mother liquor after the distilling in step (a) is benzene, toluene, xylene, or p-xylene.

14. The method according to claim 1, characterized in that the temperature for heating to dissolve in step (a) is 100-120° C.

15. The method according to claim 1, characterized in that after the distilling in step (a), the ratio of the mass of 3-carbamoylmethyl-5-methylhexanoic acid chiral resolving mother liquor to the volume of aromatic hydrocarbon solvent is 1:13-1:18 g/ml.

16. The method according to claim 1, characterized in that the concentration of the mass percentage of the alkali liquor in step (b) is 20-30%.

17. The method according to claim 1, characterized in that the solvent for extracting in step (c) is selected from n-hexane, cyclohexane, n-heptane, toluene, ethyl acetate or ethyl ether.

18. The method according to claim 1, characterized in that the alkali liquor in step (b) is aqueous solution of sodium hydroxide, sodium carbonate, potassium carbonate, and/or potassium hydroxide.

\* \* \* \* \*